US010792444B2

(12) United States Patent
Stuart et al.

(10) Patent No.: US 10,792,444 B2
(45) Date of Patent: Oct. 6, 2020

(54) DOSE INDICATOR OR DOSE COUNTER

(71) Applicant: KINDEVA DRUG DELIVERY L.P., St. Paul, MN (US)

(72) Inventors: Adam J Stuart, Loughborough (GB); Stephen J Howgill, Leicestershire (GB)

(73) Assignee: Kindeva Drug Delivery L.P., St. Paul, MN (US)

( * ) Notice: Subject to any disclaimer, the term of this patent is extended or adjusted under 35 U.S.C. 154(b) by 928 days.

(21) Appl. No.: 14/904,321

(22) PCT Filed: Jul. 8, 2014

(86) PCT No.: PCT/US2014/045694
§ 371 (c)(1),
(2) Date: Jan. 11, 2016

(87) PCT Pub. No.: WO2015/006292
PCT Pub. Date: Jan. 15, 2015

(65) Prior Publication Data
US 2016/0136365 A1    May 19, 2016

(30) Foreign Application Priority Data

Jul. 11, 2013  (GB) .................................. 1312448.2

(51) Int. Cl.
*A61M 15/00*    (2006.01)
*G06M 1/04*    (2006.01)

(52) U.S. Cl.
CPC ...... *A61M 15/0075* (2014.02); *A61M 15/009* (2013.01); *A61M 15/0073* (2014.02); *G06M 1/04* (2013.01); *G06M 1/042* (2013.01)

(58) Field of Classification Search
CPC ...... A61M 15/00; A61M 15/0001–001; A61M 15/0013–0026; A61M 15/0028–0038;
(Continued)

(56) References Cited

U.S. PATENT DOCUMENTS 5,349,945 A   9/1994  Wass
5,421,482 A   6/1995  Garby
(Continued)

FOREIGN PATENT DOCUMENTS

FR    2857770    1/2001
GB    2385640    8/2003
(Continued)

OTHER PUBLICATIONS

International Search Report for PCT International Application No. PCT/US2014/045694, dated Oct. 16, 2014, 3 pages.

*Primary Examiner* — Samchuan C Yao
*Assistant Examiner* — Ned T Heffner
(74) *Attorney, Agent, or Firm* — Mueting Raasch Group

(57) ABSTRACT

A dose indicator or dose counter is disclosed which includes an indexable first display unit indexable about a first display axis, an indexable second display unit indexable about a second display axis, the second display axis being transverse to the first display axis, and a chassis comprising a chassis frame, a displacement portion comprising a drive means to engage the first display unit, and at least one hinge means directly or indirectly connecting the displacement portion and chassis frame. The drive means is preferably configured to index the dose indicator. The dose indicator/counter has a small number of components yet is effective, reliable and compact.

29 Claims, 13 Drawing Sheets

(58) Field of Classification Search
CPC ... A61M 15/004–0043; A61M 15/0045–0051;
A61M 15/0056; A61M 15/006; A61M
15/0065; A61M 15/0068–0083; A61M
15/0091–0098; A61M 15/06; A61M
15/08–085; A61M 2202/064; A61J
1/2006–2017; A61K 9/14; G06M 1/00;
G06M 1/02–028; G06M 1/04–086; G06M
1/10–385
See application file for complete search history.

(56) References Cited

U.S. PATENT DOCUMENTS

| | | | |
|---|---|---|---|
| 5,881,719 A * | 3/1999 | Gottenauer | A61M 15/0045 |
| | | | 128/203.15 |
| 6,752,153 B1 | 6/2004 | Eckert | |
| 7,806,295 B2 | 10/2010 | Stradella | |
| 7,828,172 B2 | 11/2010 | Stradella | |
| 8,662,381 B2 | 3/2014 | Kaar et al. | |
| 2009/0173346 A1 * | 7/2009 | Stuart | A61M 15/009 |
| | | | 128/203.12 |
| 2010/0313884 A1 * | 12/2010 | Elliman | A61M 15/009 |
| | | | 128/203.12 |
| 2013/0074833 A1 | 3/2013 | Sieffert et al. | |

FOREIGN PATENT DOCUMENTS

| | | |
|---|---|---|
| JP | 2002-513664 | 5/2002 |
| WO | WO 1992-09324 | 6/1992 |
| WO | WO 1998-52634 | 11/1998 |
| WO | WO 1999/57019 | 11/1999 |
| WO | WO 2002-091293 | 11/2002 |
| WO | WO 2007/045904 | 4/2007 |
| WO | WO 2007-124406 | 11/2007 |
| WO | WO 2010-125291 | 11/2010 |
| WO | WO 2011-071788 | 6/2011 |

* cited by examiner

DOSE INDICATOR OR DOSE COUNTER

CROSS REFERENCE TO RELATED APPLICATIONS

This application is a national stage filing under 35 U.S.C. 371 of PCT/US2014/045694 filed 8 Jul. 2014, which claims priority to GB Application No. 1312448.2, filed 11 Jul. 2013, the disclosure of which is incorporated by reference in its/their entirety herein.

BACKGROUND

The present specification relates to dose indicators or dose counters, and more particularly to dose indicators or dose counters for pressurised metered dose inhaler (pMDI) devices. The present invention also relates to actuators comprising such dose indicators/counters and to inhalers comprising such actuators.

Patients who use inhalers, such as pMDI devices, need to monitor their inhaler usage, and regulators of medicines have begun to require that some method of dose indication is included into the inhaler. Dose counters (providing a precise count of the number of doses remaining) and dose indicators (providing an indication of the number of doses remaining) for inhalers are known.

In most dose counters and dose indicators, the display is indexed each time the inhaler device is used. Many dose counters and/or dose indicators are complex, requiring a number of small mechanical parts, which may increase cost, may lead to difficulties in assembly, and may require tight dimensional tolerances.

International Publication No. WO 2011/071788 discloses dose counters for dispensers and in particular dose counters for use with metered dose inhalers.

U.S. Pat. No. 6,752,153 discloses an inhaler for aerosolization of medicament with a dose counter. The dosage counter has a first and a second counting ring and a coupling device that connects the counting rings.

International Publication No. WO 1998/52634 discloses a dosing device and in particular relates to dosing devices for drug delivery such as injectors and inhalers and a mechanism for use in such devices.

It would be advantageous to provide a dose indicator or dose counter that has fewer essential parts. It would also be advantageous if the dose indicator were designed to fit within typical existing pMDI actuators and to be compatible with existing pMDI valves.

In this specification, the term "dose indicator" is intended to refer to both dose counter devices and dose indicator devices.

SUMMARY

In a first aspect, there is provided a dose indicator comprising, an indexable first display unit indexable about a first display axis, an indexable second display unit indexable about a second display axis, the second display axis being transverse to the first display axis, and a chassis comprising a chassis frame, a displacement portion comprising a drive means to engage the first display unit, and at least one hinge means directly or indirectly connecting the displacement portion and chassis frame. The drive means is preferably configured to index the dose indicator.

This is advantageous because it provides a dose indicator/counter that has a small number of components yet is effective, reliable and compact. Furthermore, the invention allows the provision of a cheap, simple and reliable dose-by-dose counter that is capable of counting 200 doses or puffs. It may count down from 200 to 0 and is able to fit within a pMDI actuator of similar shape and comparable size to existing actuators.

The hinge means (e.g. hinge or hinges) may generally be any connecting portion including such that allows restricted but controlled relative movement of the displacement portion and the chassis frame, including relative rotational and/or translational movement.

The second display axis and the first display axis may be arranged so that they do not intersect. However, generally the second display axis will intersect the first display axis.

The second display axis may, preferably, be at an acute or an obtuse angle to the first display axis. In some circumstances, the second display axis may be substantially orthogonal to the first display axis.

Generally, the first display unit and/or the second display unit will be substantially circular in a cross-section (usually a cross section transverse, preferably generally orthogonal, to the first and/or second display axis respectively) and will be rotatably indexable about the first display axis and/or about the second display axis respectively. The term "substantially circular" in this context includes annular or disc-shaped embodiments and polygonal shapes with at least five sides.

The drive means is preferably adapted to engage the first display unit. In particular, it is preferred if the drive means is adapted to engage the first display unit on a curved path, the drive means being driven by a force from outside the circumference of the first display unit. This improves the stability of indexing because it allows freer movement of the drive means past the first display unit and reduces the risk of advancing an additional, unwanted count.

Thus, in a second aspect, there is provided a dose indicator comprising, an indexable first display unit rotatably indexable about a first display axis, and a chassis comprising a chassis frame, a displacement portion comprising a drive means to engage the first display unit, and at least one hinge means directly or indirectly connecting the displacement portion and chassis frame, wherein the drive means is adapted to engage the first display unit on a curved path, the drive means being driven by a force from outside the circumference of the first display unit. Optionally there is also an indexable second display unit, indexable about a second display axis.

Preferably, the first display unit is rotatable in a first plane transverse to the first display axis, and the curved path is at least partly outside the first plane. It is also preferred that the drive means is driven by a force that has a component generally in the first plane, the component of the force that is in the first plane being outside the circumference of the first display unit. This is advantageous because it allows that the first display unit may be of generally disc-like or polygonal (5 sides or greater) cross section with the indexing features (e.g. indexing teeth) being on the outer circumference of the unit.

Preferably, the drive means is angled into the first display unit to improve engagement and to reduce the chance of the drive means unintentionally disengaging from the first display unit.

Preferably, the chassis is moulded as a unitary piece. Preferably, the first display unit is also moulded as a unitary piece. It is also preferred if the second display unit is moulded as a unitary piece. This is advantageous because it enables the reduction of the number of parts of the dose indicator, with consequent benefits of cost and simplicity of assembly. The components of the dose indicator may therefore number just three corresponding to chassis, first display unit and second display unit. However, in some circumstances additional components may be advantageous.

It is preferred if the chassis, first display unit and second display unit are each independently designed so they may be injection moulded without the requirement for a side action in the moulding tool. This reduces flash in the moulded components.

It is preferred if the drive means is integrally comprised in the displacement portion.

In preferred embodiments, the drive means comprises a drive pawl. In some embodiments it is advantageous if the engaging end of the drive pawl is outside the cylindrical envelope of the first display unit (i.e. outside its circumference) in the rest position, and is brought within this envelope during actuation. Thus, during actuation preferably the drive pawl follows a path from outside the circumference of the first display unit.

Usually, the displacement portion will be adapted so that it may be displaced along a displacement path that is preferably at least partly transverse to the first display axis. It is preferred if the displacement path is at least partly arcuate. This may be achieved, for example, if the drive means is located on the displacement portion at a position remote from the hinge or hinges, preferably at a position distal to the hinge or hinges. The hinges may be configured for substantially pivotal (rotational) movement of the displacement portion.

Usually, the displacement portion will comprise at least one press member that acts as an interference portion for interference with the valve during actuation. The press member or members may for example be a press knuckle or press knuckles. It is advantageous if the contact points (e.g. press knuckles) between the valve and the displacement portion include points that are radially in different directions from the valve stem, as this helps to compensate for effects of the patient tilting the canister slightly during actuation. Thus, preferably there are two or more contact points (e.g. press knuckles) distributed on the displacement portion.

The dose indicator will usually further comprise at least a first display non-return means, the first display non-return means being preferably at least partly located on the chassis frame. The non-return means may be for example a frictional non-return means, but in a preferred embodiment the first display non-return means comprises a non-return arm adapted to interact with one or more detents on the first display unit.

The chassis preferably further comprises at least one return means. The return means will usually comprise at least one spring. Preferably, the at least one spring comprises a leaf spring, preferably a curved leaf spring. The at least one return means (preferably a curved leaf spring) will usually directly or indirectly connect the displacement portion and chassis frame, preferably at a position remote from the hinge or hinges.

Usually, the first and/or the second display unit will be adapted to index through between 5 and 25 indicia, preferably 8 to 12 indicia.

The dose indicator may comprise a first display unit mounting means for mounting the display unit on the chassis frame so that it is indexable about the first display axis.

The internal profile of the first display unit may include an axle bearing and the chassis may include an axle with an external profile designed to engage closely with the axle bearing to allow relative rotational movement without wobble. This may be achieved by close circumferential engagement of the internal profile of the first display unit and the external profile of the first display unit axle over most of the circumference corresponding to positions on the first display unit axle that are axially separated by some distance. This distance is preferably greater than the thickness of the portion of the first display unit that bears indicia.

The first display unit axle may be substantially cylindrical, or it may have cylindrical sections of different diameter. For example the section closer to the first display unit's indicia may have the larger diameter. The first display unit axle may have a lead-in surface at the distal end to facilitate placing of the first display unit. This first display unit axle may be configured to hold the first display unit in position and to prevent its axial translation along the first display unit axle, e.g. by the provision of circumferential detents.

Usually, in embodiments of the invention, the first display unit is a units display unit.

Preferably, the second display unit is a tens display unit.

In preferred embodiments the first display unit comprises a drive arm adapted to index the second display unit. This is particularly suited to embodiments in which the second display unit is a tens display unit.

An angled edge may be provided on the trailing side of the drive arm and/or the indexing teeth of the second display unit may be provided with angled leading edges. This reduces the chances of a double second (e.g. tens) count occurring whilst maximizing the overlap between the drive arm and indexing teeth. A rounded leading edge may be provided on the leading edge of the drive arm. This ensures that the point contact with an indexing tooth has a high incident angle for most of an indexing movement of the second display unit.

In some embodiments the first display unit has a substantially circular cross section, preferably a cross section on a plane transverse (more preferably substantially orthogonal) to the first display axis.

In some embodiments the second display unit has a substantially circular cross section, more preferably a substantially annular cross section. It is preferred if the cross section is on a plane transverse (more preferably substantially orthogonal) to the second display axis.

In preferred embodiments, the first and/or the second display unit comprises a zero stop means. It is particularly preferred that the second display unit comprises a zero stop means to stop the second display unit from advancing beyond the zero count (e.g. of ten if the second display units is a tens display unit) corresponding to a nearly empty inhaler, and the second display unit is preferably further configured to prevent indexing of the first display unit beyond the ensuing zero units count. This configuration of the stop means may be achieved by using positive engagement between the first (e.g. the units) display unit and the second (e.g. tens) display unit. In embodiments where the first and/or the second display unit comprises a zero stop means, the drive member may be configured to deflect or collapse to allow continued use of the inhaler after the displayed overall count has reached zero.

Preferably, the zero stop means interacts with a stop arm located on the chassis. Advantageously, the chassis comprises polyoxymethylene (i.e. POM, acetal).

The polyoxymethylene is preferably in homopolymer form.

In a third aspect, the invention provides an actuator for an inhaler, the actuator comprising a dose indicator as discussed in the first or second aspect.

In a fourth aspect, the invention provides an inhaler comprising an actuator as discussed in the third aspect.

The dose indicator of the present invention is of simple construction, whilst being robust and reliable in its indication of doses. It is suitable for use in a pressurized metered dose inhaler (pMDI) or other dispensing devices (e.g. dry powder inhalers, aqueous pump dispensers) to indicate usage (e.g. number of doses used or number of doses remaining) by means of numbers and/or coloured regions or other indicia in its display. Typically doses are counted downwards, and an indication of when the inhaler canister needs to be replaced may be provided in addition to an indication of the number of doses that have been dispensed.

When adapted for a pMDI, the dose indicator may be of a suitable size and configuration to fit into existing inhaler actuators, including breath actuated actuators or actuators with breath coordination means incorporated, without appreciable changes to the dimensions or shape of the existing actuator designs. Actuators will typically be provided with a window for viewing the dose indication or count.

BRIEF DESCRIPTION OF THE DRAWINGS

So that the present specification may be more completely understood, reference is made to the accompanying drawings in which like elements are given like reference numerals (with the addition of 100 or multiples of 100 to the numerals of different embodiments).

DETAILED DESCRIPTION

This invention relates to a two-component (with an optional third component) dose indicator for a pMDI. The indicator may be indexed by the displacement generated when a patient actuates a pMDI valve.

In the embodiment illustrated in FIGS. 1 to 7, the dose counter 1 comprises a dose-by-dose counter for a pMDI (that is capable of being configured to count down from 200 to 0) which comprises a chassis 2, a units display unit 33 and an optional tens display unit 42. The dose counter 1 can be inserted into a standard pMDI actuator.

Figure 1:
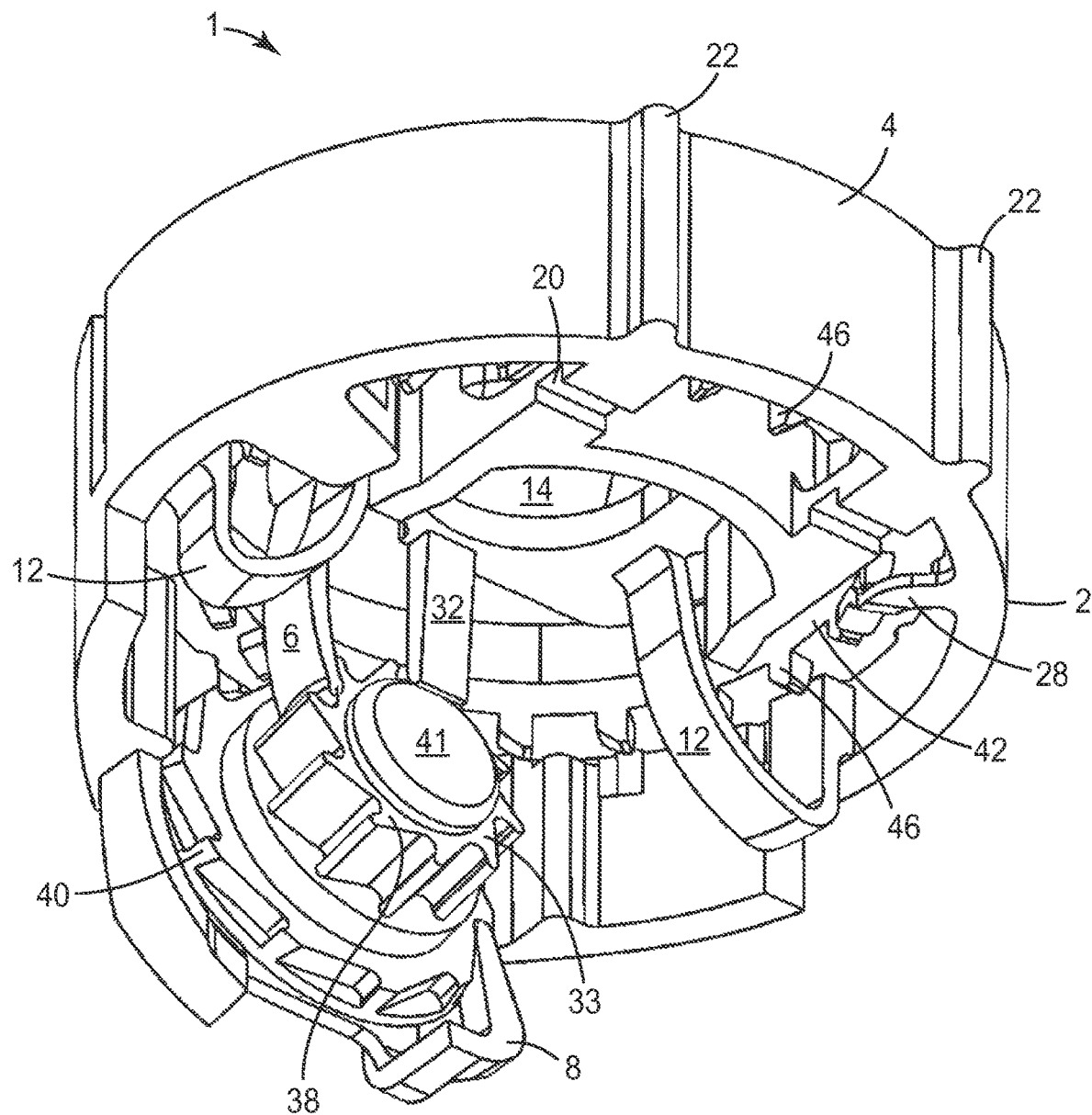
FIG. 1 shows a bottom perspective view of an exemplary dose indicator.
Figure 7:
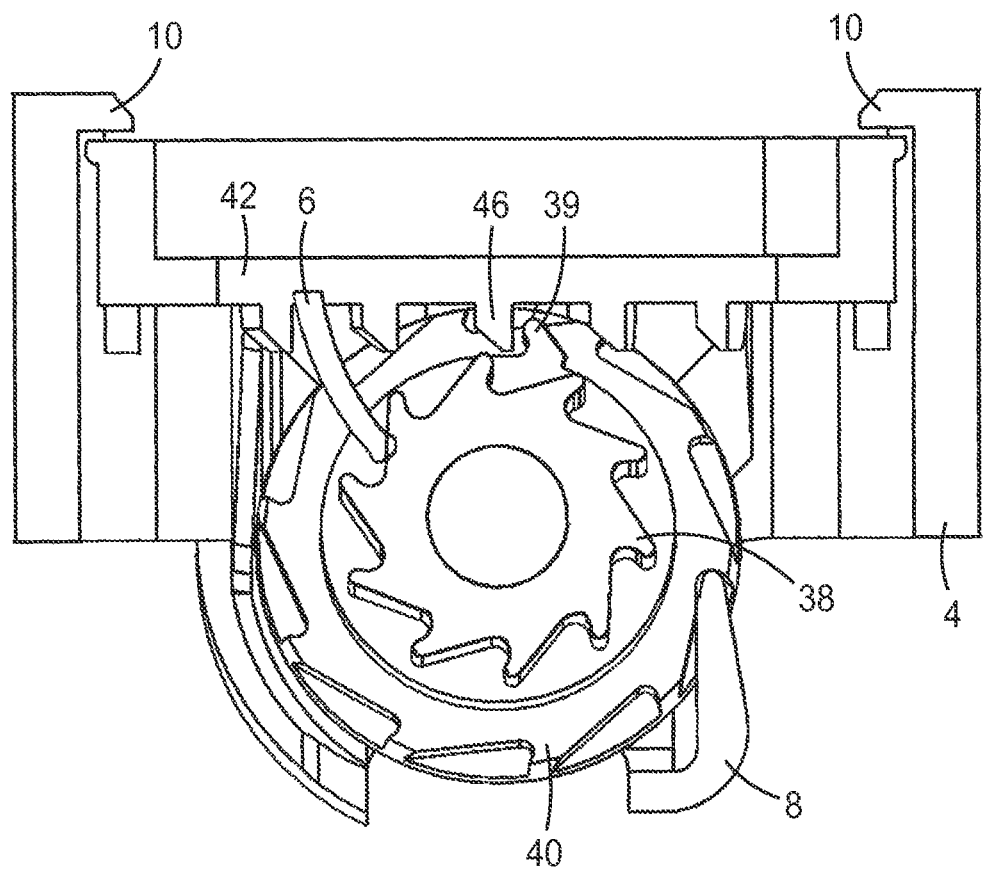
FIG. 7 shows a side view of the dose indicator of FIG. 1, illustrating its operation.

As shown in FIG. 1 and FIG. 7, a dose counter 1 comprises a chassis 2 with a chassis frame 4 of generally annular form. The annular form of the chassis frame 4 is designed to fit snugly into an inhaler actuator to provide support and to prevent deformation in use. Optionally the support may be enhanced by one or more ledges on the actuator for seating a horizontal surface of the chassis, or ribs/grooves to prevent deformation and relative rotation of the chassis frame in the actuator. The chassis 2 incorporates a number of features including springs, hinges and indexing features that are used to actuate and reset the device. The features are formed integrally (i.e. moulded in a unitary piece) with the chassis 2.

The dose counter 1 also comprises a units display unit 33 that comprises a units display unit boss 41 and a series of units display unit indexing teeth 38. A drive pawl 6 formed integrally with the chassis 2 contacts the indexing teeth 38 and indexes the teeth when chassis 2 is pressed against by a valve of a medicament canister pressing downwards on indexing knuckles 26 (not visible in FIG. 1; see FIG. 2) on the top side of the chassis 2. When pressed downwards, the displacement plate 19 (see FIG. 2) of the chassis 2 moves downwards and hinges 20, integrally formed with the chassis frame 4 and displacement plate 19, deform. Spring arms 12 return the chassis 2 to its original position after indexing.

A non-return arm 8 also formed integrally with the chassis 2 contacts a series of non-return teeth 40 arranged coaxially with the indexing teeth 38, and prevents backwards movement of the units display unit 33. A units display unit stop arm 32 integrally formed with the chassis 2 is positioned adjacent to the units display unit boss 41 and guards against the units display unit 33 jumping off its mounting.

The dose counter 1 also comprises an optional tens display unit 42 in the form of a ring with tens display unit indexing teeth 46 indexed by the tens display unit drive tooth 39 (not visible in FIG. 1; see FIG. 7) and generally prevented from backwards movement by the tens display unit non-return arm 28.

Lugs 22 reduce rotation of the dose counter 1 when mounted in the actuator in such a way as to allow the stem post of the actuator to pass through stem post aperture 14.

Figure 2:
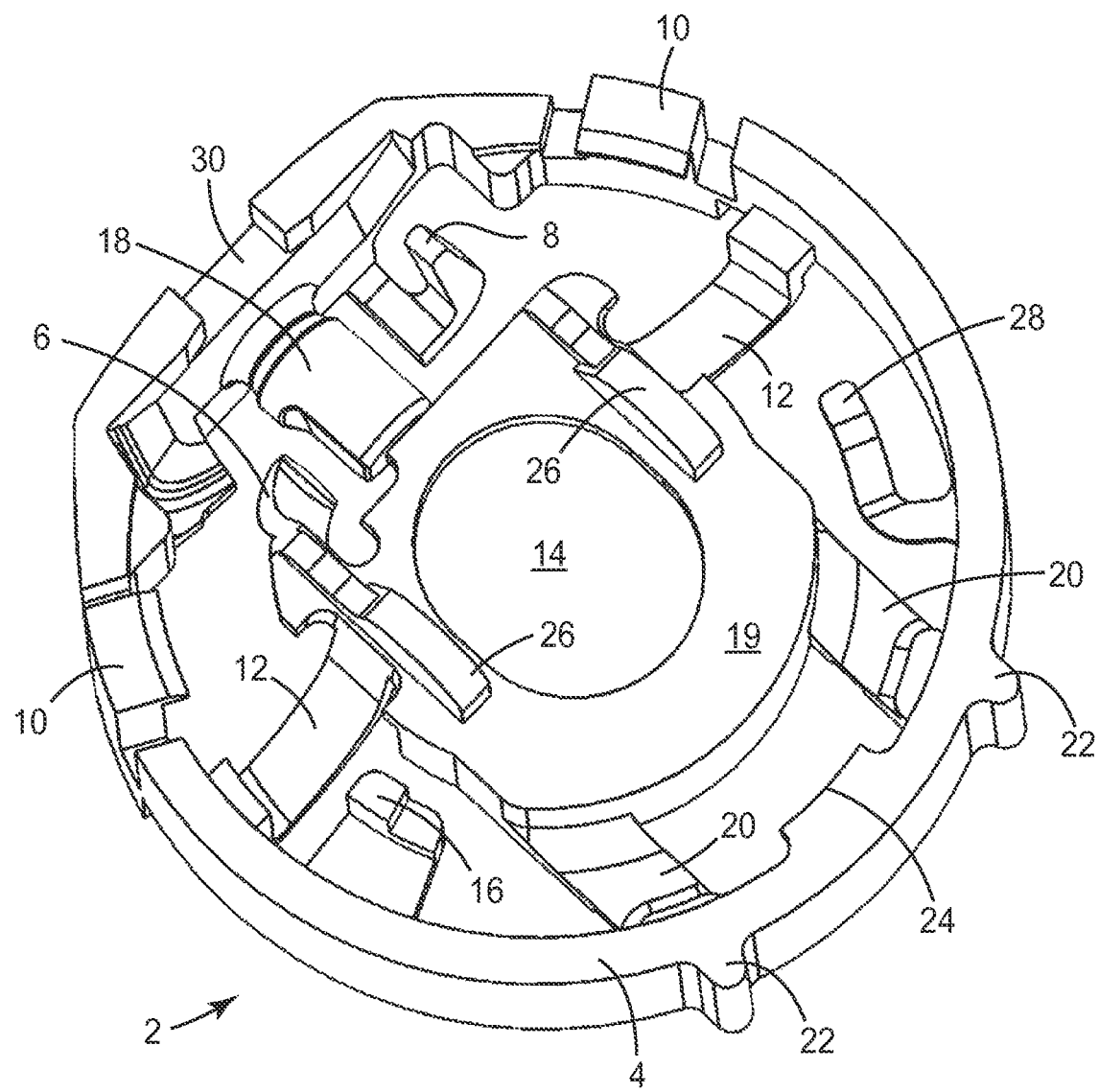
FIG. 2 shows a top perspective view of a chassis of the dose indicator of FIG. 1.
Figure 3:
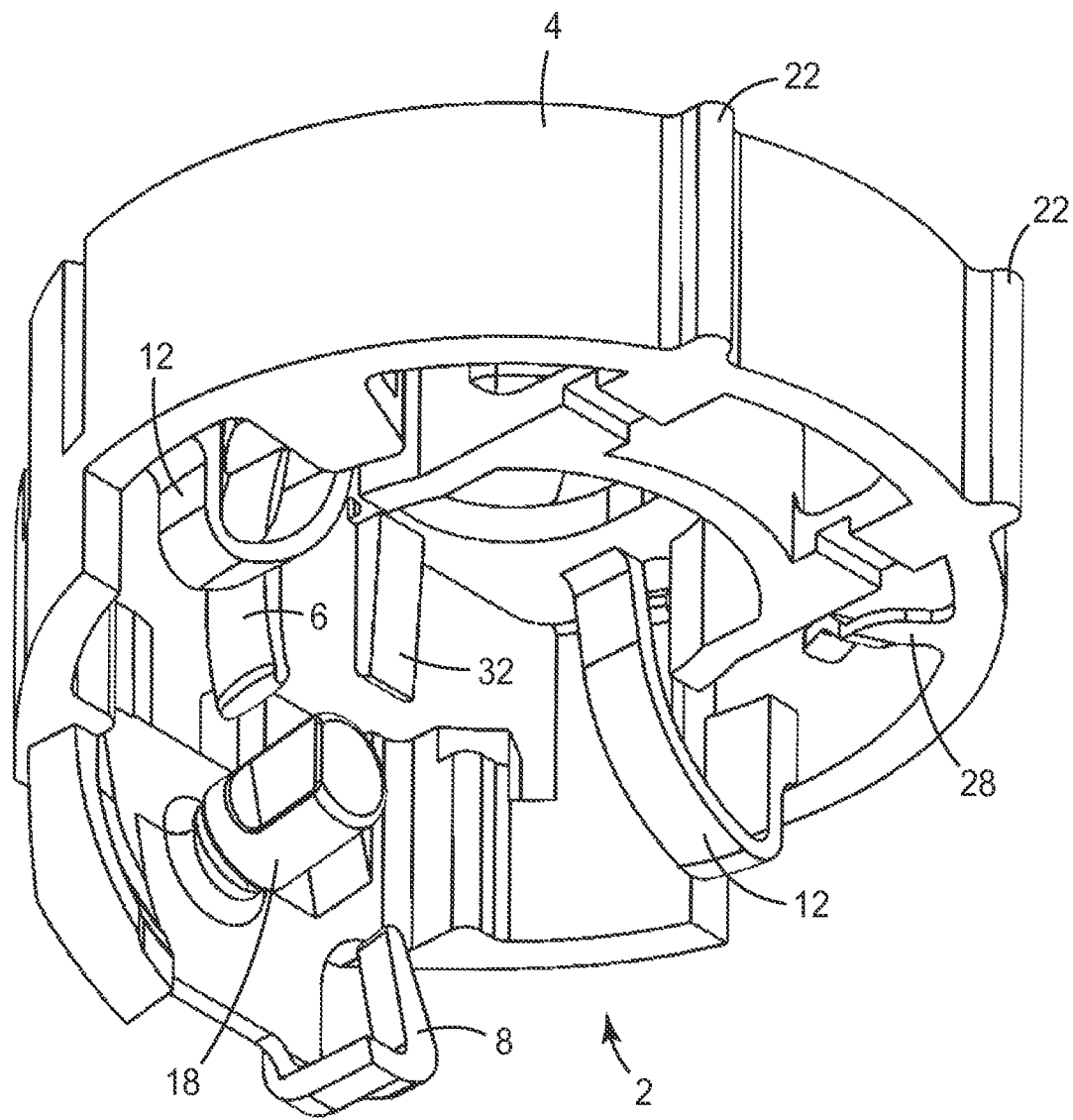
FIG. 3 shows a bottom perspective view of the chassis of the dose indicator of FIG. 1.

FIGS. 2 and 3 show the chassis 2 from a top view and a side bottom view respectively. In addition to the features visible in FIG. 1, the chassis 2 comprises indexing knuckles 26 (see FIG. 2) that are contacted by the valve of a medicament canister when it is displaced downwards to actuate the metered dose valve to dispense a metered dose. As discussed above, upon actuation the displacement plate 19 moves downwards and the hinges 20 deform. The spring arms 12 are resilient and resist displacement and return the displacement plate 19 to its original position after actuation.

Thus, an indexing element is attached to a displacement plate 19 that is anchored to a chassis frame 4 at one end by two hinges and at the other end by two spring arms 12 that are also anchored to the chassis frame 4. The two spring arms 12 have a long active length in order to reduce stress concentration. This is advantageous because it reduces strain in the springs over time.

Having the spring arms 12 separate from the hinges is also advantageous, as each feature is only required to perform a single function.

In alternative embodiments, the hinges could be used to provide the spring force, but due to a short active spring length the stresses and strain in the hinges would be higher.

In an alternative embodiment, the hinge means may be provided by one or more springs.

The units display unit 33 is mounted on the units display unit axle 18, which is angled at an acute angle with respect to the chassis 2 to take account of the arcuate movement of the drive pawl 6 owing to its position distal to the hinges 20 on the displacement plate 19. The chassis frame 4 includes tens display unit clips 10 and tens display unit locating ledge 24 to mount the tens display unit 42, and zero stop arm 16.

Figure 4:
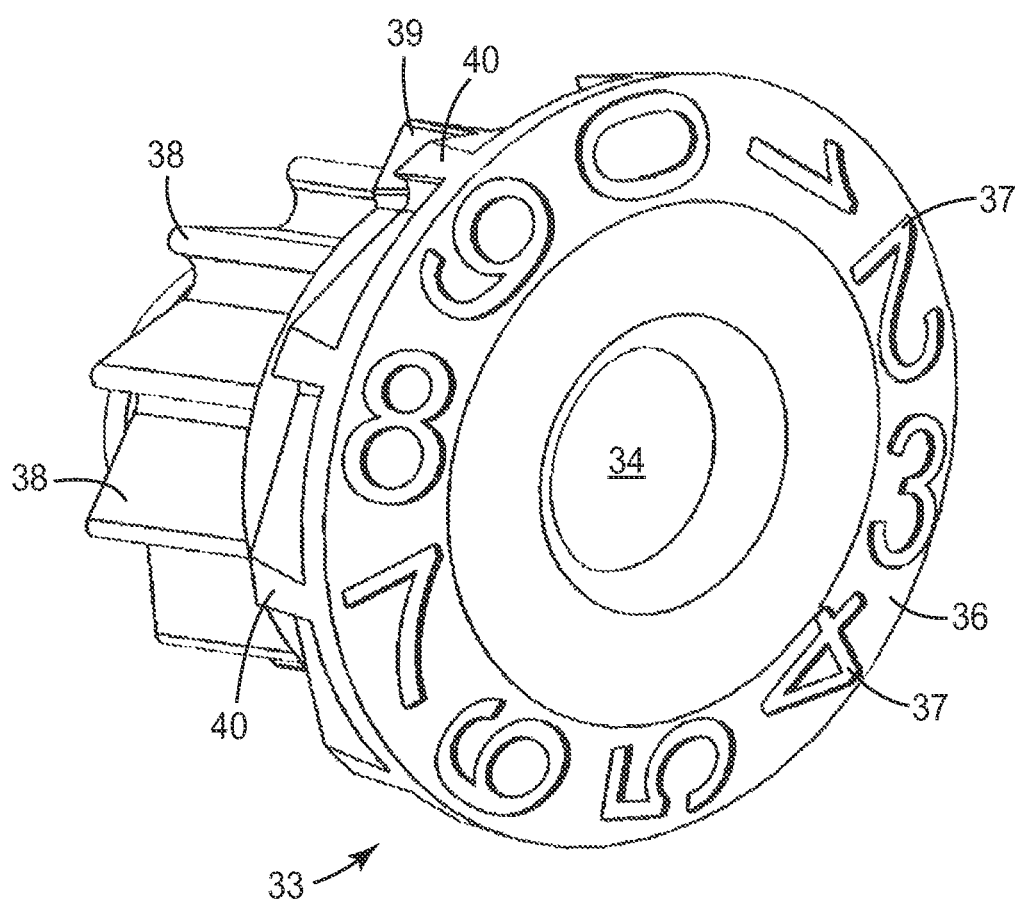
FIG. 4 shows a side perspective view of the units display unit of the dose indicator of FIG. 1.
Figure 5:
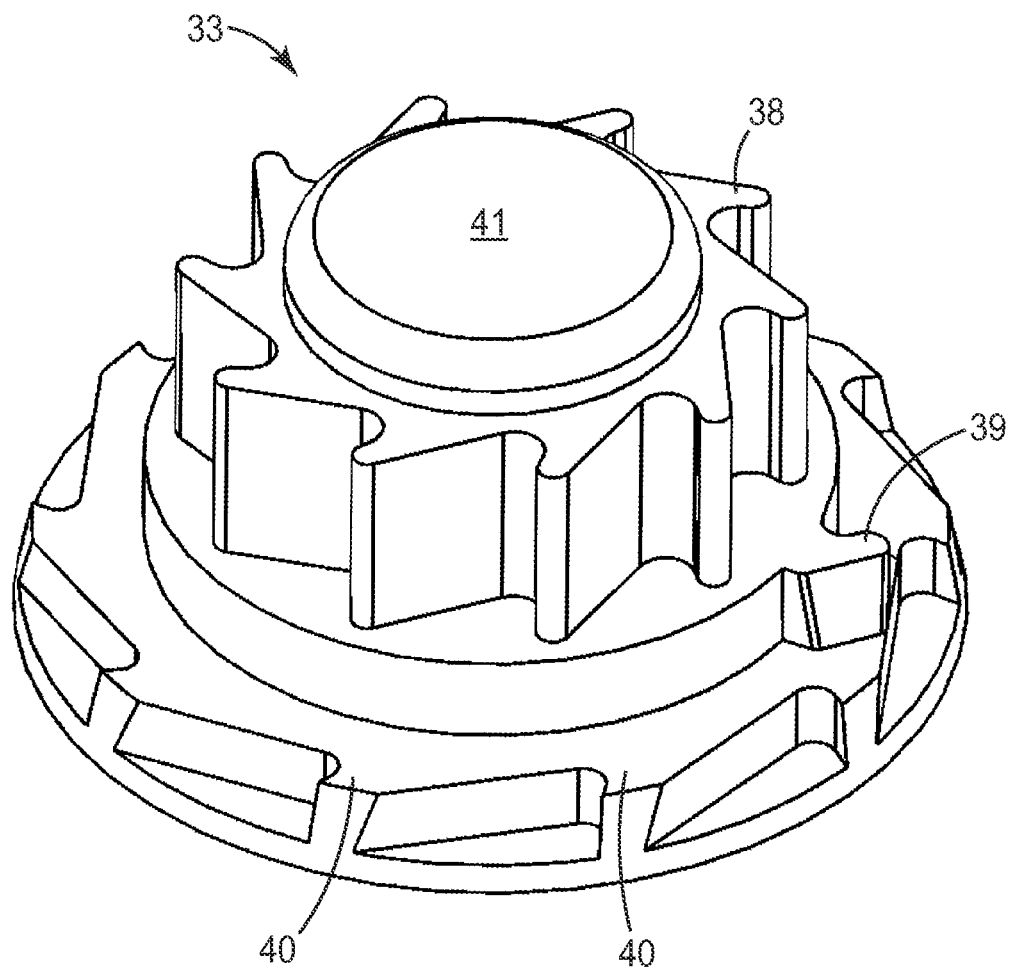
FIG. 5 shows a reverse side perspective view of the units display unit of the dose indicator of FIG. 1.

FIGS. 4 and 5 show the units display unit 33. The units display unit 33 is generally circular in end view and comprises two coaxial sets of gear teeth: units display unit indexing teeth 38 and units display unit non-return teeth 40. The units display unit indexing teeth 38 interact with the drive pawl 6 when the units display unit 33 is mounted on the chassis 2. The units display unit non-return teeth 40 interact with the non-return arm 8 when the units display unit 33 is mounted on the chassis 2, thereby preventing return of the units display unit 33 after an indexing stroke.

The profiles of the indexing teeth 38 and non-return teeth 40 have been designed with a hooked edge that prevents or reduces the chance of the pawls or arms from disengaging or slipping off the tooth during actuation.

The axle bearing 34 of the units display unit 33 is mounted on the units display unit axle 18 of the chassis 2. The internal profile of the units display unit 33, including axle bearing 34, and the external profile of the units display unit axle 18 are designed to engage closely to allow relative rotational movement without wobble. This may be achieved by close circumferential engagement of the internal profile of the units display unit 33 and the external profile of the units display unit axle 18 over most of the circumference corresponding to positions on the units display unit axle 18 that are axially separated by some distance. This distance is preferably greater than the thickness of the portion of the units display unit 33 that bears indicia. The units display unit axle 18 may be substantially cylindrical, or it may have cylindrical sections of different diameter such that the proximal section is the larger diameter section. The units display unit axle 18 may have a lead-in surface at the distal end to facilitate placing of the units display unit 33. The units display unit 33 may be prevented from axial translation by the units display unit stop arm 32 protruding from the displacement plate 19.

An advantage of embodiments of the invention is achieved because the drive means is adapted to engage the first display unit on a curved path, the drive means being driven by a force starting from outside the circumference of the first display unit. This improves the stability of indexing when the units display unit 33 is mounted on the chassis 2 because it allows freer movement of the drive pawl 6 past the display unit 33 without advancing an additional, unwanted count. In the rest position, the drive pawl 6 sits above the first of the units display unit 33 indexing teeth 38 and the non-return arm 8 is engaged with the first of the units display unit non-return teeth 40 (that prevent reverse rotation of the units display unit 33).

Preferably the drive pawl 6 and non-return arm 8 act at opposite sides of the units display unit axle 18, which allows less stringent tolerance requirements for the dimensions of the axle 18 and axle bearing 34.

The units display unit 33 has on its face a units display surface 36 with a plurality (ten numerals 0 to 9 in the illustrated embodiment) of units indicia 37 to indicate the remaining doses.

Between the units display unit indexing teeth 38 and units display unit non-return teeth 40, there is a tens display unit drive tooth 39 that, when the tens display unit is fitted to the dose indicator, drives the indexing teeth of the tens display unit once per cycle of the units display unit 33. In the embodiment of FIG. 4 with ten drive teeth 38, the tens display unit would be driven once every 10 cycles.

The units display unit 33 has been designed such that it can be injection moulded without the requirement for a side action in the moulding tool. This is advantageous, as it will reduce the capital cost of tooling and reduce the risk of flash on components.

Figure 6:
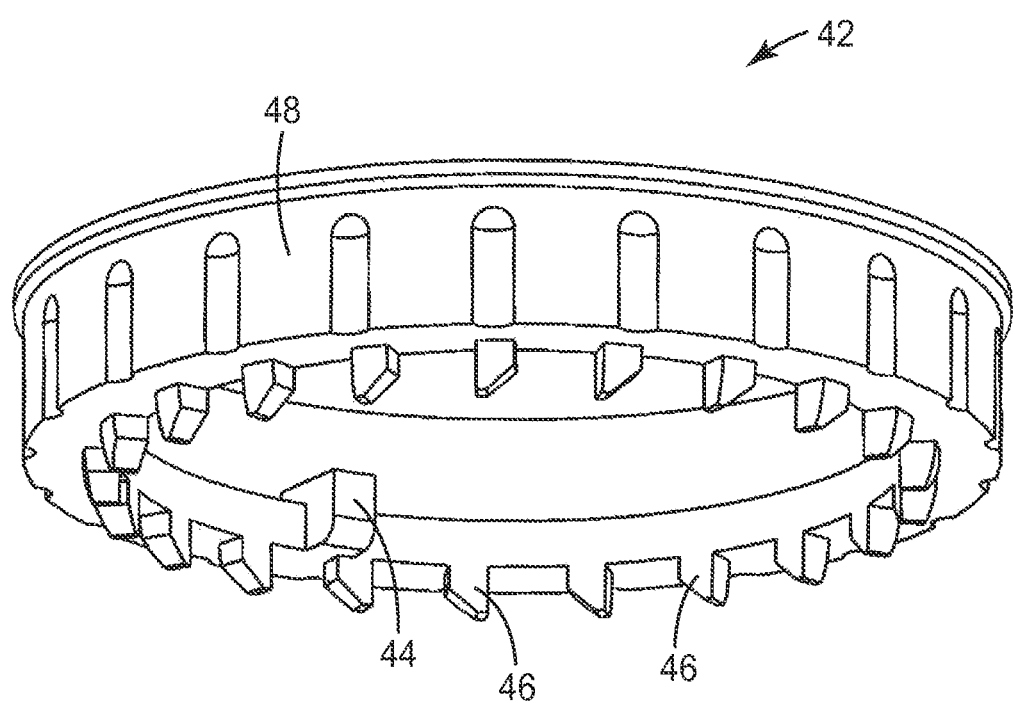
FIG. 6 shows a bottom perspective view of the tens display unit of the dose indicator of FIG. 1.

FIG. 6 shows the tens display unit 42 which is of generally annular form with 21 tens display unit indexing teeth 46 evenly distributed around the circumference of the tens display unit 42. The tens display unit drive tooth 39 has been given a rounded leading edge to ensure that the point contact with the tens display unit indexing teeth 46 has a high incident angle for as long as possible. An angled edge has been provided on the trailing side of the drive tooth 39 and the leading edges of the tens display unit indexing teeth 46 to reduce the chances of a double tens count occurring whilst maximizing the overlap between these teeth.

A zero stop 44 (in the form of a boss) protrudes from the tens display unit 42 and interacts with the zero stop arm 16 of the chassis 2 at the end of the life of the dose indicator i.e. when the maximum number of counts has been made, e.g. when the displayed indication reaches zero.

The tens display unit 42 has a tens display unit display surface 48 which rotates as the tens display unit 42 is indexed. FIG. 6 shows the tens display unit display surface 48 as having a series of indentations 49. In a more preferred embodiment, these would be replaced by tens indicia (not shown), e.g. in the form of a sequence of numerals "20", "19", . . . down to either "00" or "0" or a blank. These numerals, and those of the units indicia 37, may advantageously be produced by hot foil printing, moulding, embossing, laser marking, or other suitable means. A viewing cut out 30 in the chassis frame 4 of the chassis 2 allows the juxtaposition of the indicia on the tens display unit 42 and those from the units display unit 33 to be seen, such that together they display the count or indication of doses (e.g. of remaining doses).

The tens display unit 42 has a rim on its outermost edge which acts as a bearing surface whilst ensuring that the printed display cannot rub against the inside wall of the chassis 2. The tens display unit 42 is located centrally in the chassis 2 by the bearing rim on the outermost surface. It is located axially by a series of clip and location features 10, 24 on the chassis 2.

The tens display unit non-return arm 28 interacts with the tens display unit indexing teeth 46 and prevents rotation in the reverse direction and restricts rotation in the drive direction except when receiving an impulse from the tens display unit drive tooth 39 on the units display unit 33.

The tens display unit 42 has been designed such that it can be injection moulded without the requirement for a side action in the moulding tool. This is advantageous, as it will reduce the capital cost of tooling and reduce the risk of flash on components. To assemble the dose counter 1, the units display unit 33 is mounted on the units display unit axle 18 on the chassis frame 4. The tens display unit 42 is then hooked under the tens display unit locating ledge 24 and pushed past the two tens display unit clips 10. Once assembled, the dose counter 1 can then be inserted into an actuator as an assembled unit.

FIG. 7 shows the dose counter part way through actuation. During operation of the dose counter 1 upon actuation of the pMDI valve, the displacement plate 19 bends at its hinges and follows a generally arcuate displacement path. The drive pawl 6 also follows an arcuate path. The drive pawl 6 is angled into the units display unit indexing teeth 38, to further help secure engagement and to reduce the chance of the drive pawl 6 unintentionally disengaging from the units display unit indexing teeth 38.

The engagement of the drive pawl 6 with the units display unit indexing teeth 38 advances the display of the units display unit 33 by one count, and the drive pawl 6 then continues its travel as far as it continues to be driven by the user, up to the limit of travel of the pMDI valve. The rotation of the units display unit 33 by one count results in the non-return arm 8 being forced to flex and to ride over the next one of the units display unit non-return teeth 40.

On the return stroke, the spring force of the spring arms 12 causes the drive pawl 6 to return to its original, rest position. The non-return arm 8 engages with the next of the units display unit non-return teeth 40, thus preventing reverse rotation of the units display unit 33. Since the units display unit 33 is unable to rotate, the drive pawl 6 is forced to ride over the next of the units display unit indexing teeth 38 and return to its rest position.

On a tens count (e.g. for a displayed count changing from "190" to "189"), as the counter is indexed the rotation of the units display unit 33 causes the tens display unit drive tooth 39 (on the units display unit 33) to engage with tens display unit indexing teeth 46. The tens unit display unit non-return arm 28 resiliently distorts under the driving force, and once the stroke is completed it detains the tens display unit 42 on the next of the tens display unit indexing teeth 46.

Once the dose counter 1 reaches a display of zero, the zero stop arm 16 on the chassis frame 4 and zero stop 44 on the tens display unit 42 come into engagement and prevent further rotation of the tens display unit 42. Interference between the last of the tens display unit indexing teeth 46 and the tens display unit drive tooth 39 on the units display unit 33 in turn prevents the units display unit 33 from rotating further. Due to the resilient flexibility in the chassis 2, spring arms 12 and drive pawl 6, the inhaler can still be actuated once the stop-at-zero features become engaged.

The indexing of the units display unit 33 and tens display unit 42 occurs on the down-stroke of the actuation. This is advantageous, as work on the dose counter 1 is being carried out by the user (rather than, for example, by spring return force, which would be limited). This leads to a more reliable device, as the function of the spring arms 12 is only to reset the counter.

Due to the properties required for the spring arms and ratchets, the chassis 2 is preferably made from polyoxymethylene (also known as POM or acetal) or material with similar properties (high stiffness, low friction and good dimensional stability). Preferably the acetal is an acetal homopolymer. POM and materials with similar properties tend to be opaque hence the need for a cut out portion in the chassis and corresponding window in the actuator body so that the indicia are visible.

The chassis 2 has been designed such that it can be injection moulded without the requirement for a side action in the moulding tool. This is advantageous, as it reduces the capital cost of tooling and reduces the risk of flash on components.

Figure 8:
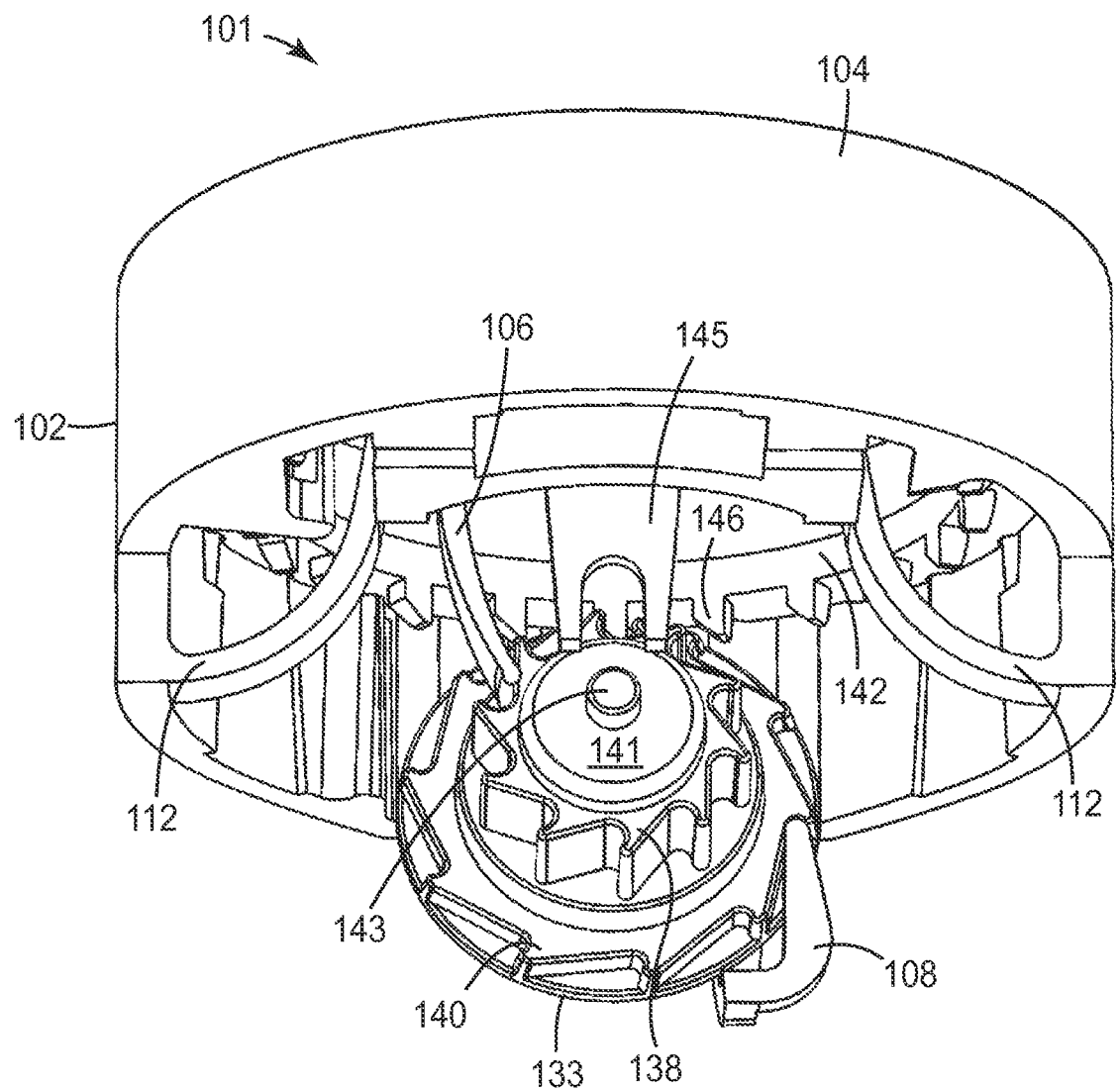
FIG. 8 shows a perspective view of a second exemplary dose indicator.

FIG. 8 shows an alternative embodiment of a dose indicator 101 part way through actuation, comprising a chassis 102 with a chassis frame 104 of generally annular form. The embodiment of FIG. 8 also has spring arms 112, a drive pawl 106 driving the indexing teeth 138 of a units display unit 133, and a tens display unit 142 with tens display unit indexing teeth 146. The units display unit has non-return teeth 140 that interact with the non-return arm 108 of the chassis 102 and, in this embodiment, a boss protrusion 143 on the boss 141 which on pressing down of the displacement plate 119 during actuation interacts with a forked deadstop 145 moulded integrally with the displacement plate 119. This is advantageous because is prevents the springs 112 and hinges being overstressed during use, e.g. if the user presses with a force significantly in excess of that needed to operate the dose indicator and to actuate the valve.

Figure 9:
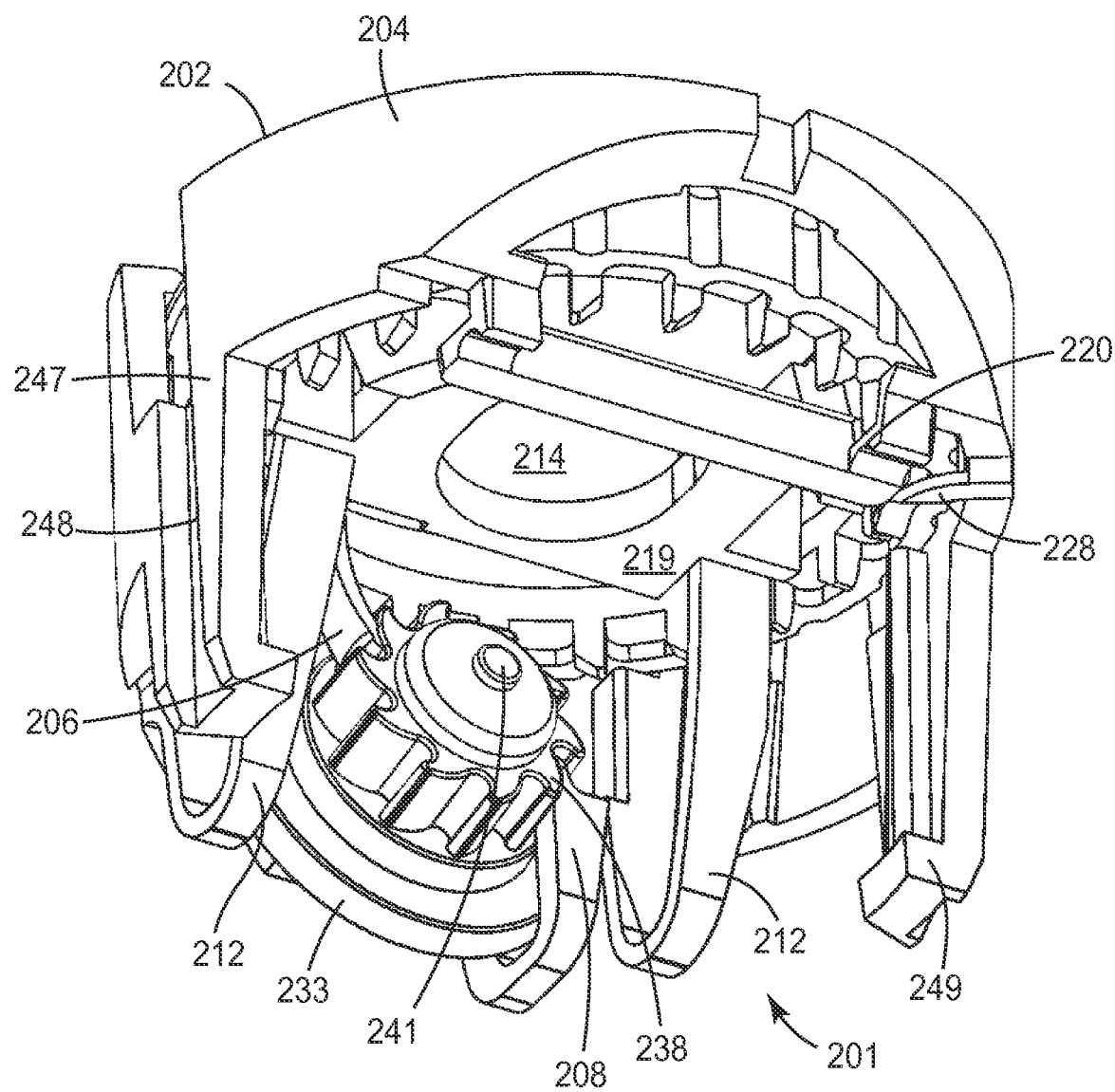
FIG. 9 shows a bottom perspective view of a third exemplary dose indicator.

As shown in FIG. 9, a third embodiment of a dose counter 201 according to the invention comprises a chassis 202 with a chassis frame 204 of generally annular form. The chassis 202 incorporates a number of features including springs, hinges and indexing features that are used to actuate and reset the device. These features are formed integrally with the chassis 202.

The dose counter 201 is somewhat similar to that shown in FIG. 1, so only those features that differ will be described.

Figure 11:
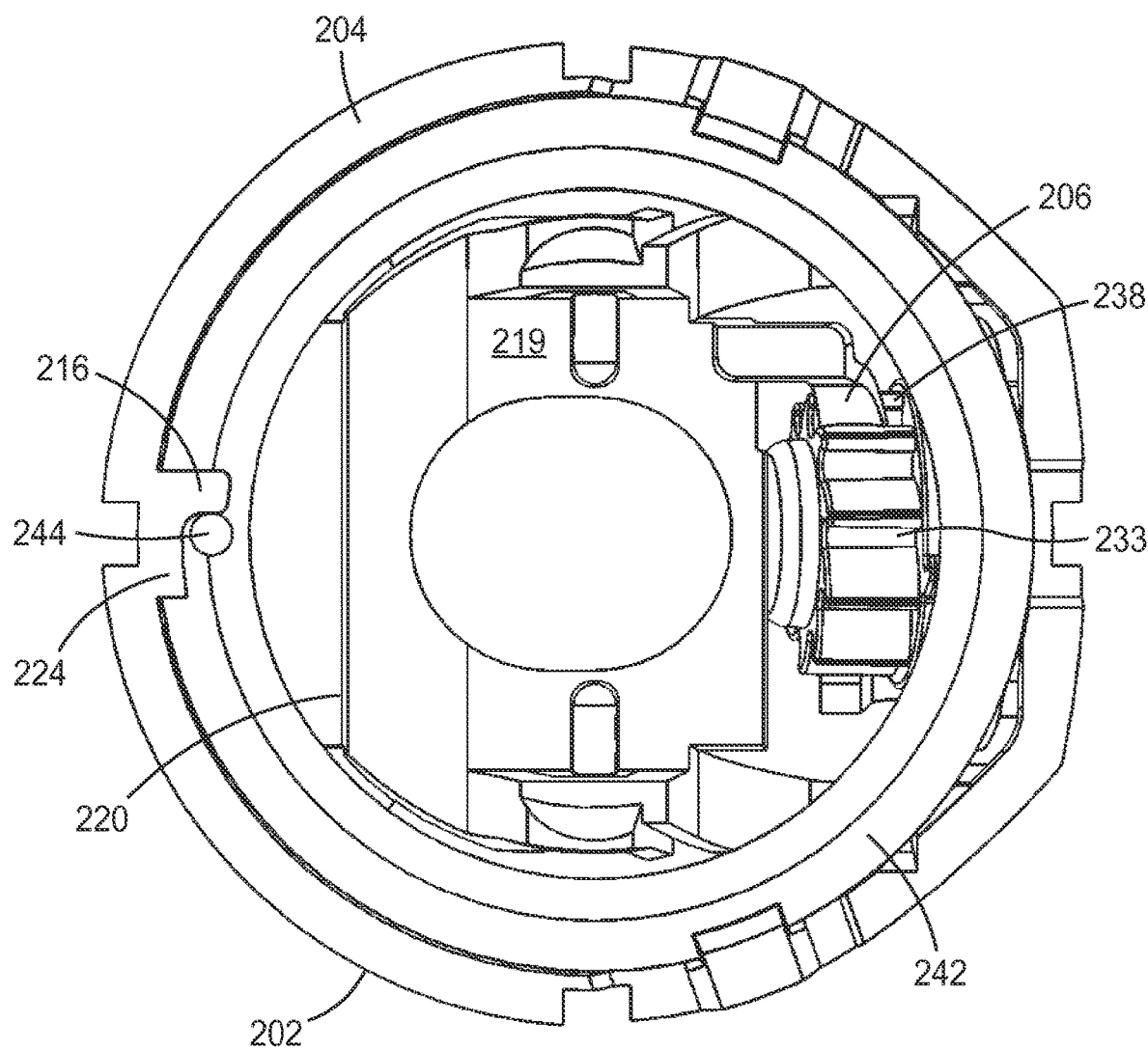
FIG. 11 shows a top view of the third exemplary dose indicator

A displacement plate 219 is attached to the chassis 202 by two hinges 220. The hinges 220 have bridge-shaped features to direct most of the flexing to the thinner regions at the apex of each bridge. The displacement plate 219 is also attached to the chassis 202 by two spring arms 212, joined to the chassis 202 on the opposite side to the hinges, and joined to the displacement plate 219 by lateral extensions to the plate that are just to the side of the stem post aperture 214 further from the hinges 220. The spring arms 212 are designed to flex transversely to the axis of the hinges, to provide additional return force for the displacement plate 219 without any twisting of the spring arms. The hinges 220 are slightly further forward towards the units display unit 233 than are the hinges 20 of the embodiment in FIG. 1: this reduces the distance of pMDI metering valve stem movement needed to cause the dose counter to index. The displacement plate 219 has an integral drive pawl 206, and is formed integrally with the spring arms 212, hinges 220 and chassis 202. The displacement plate 219 does not have a units display unit stop arm, however, as this feature 216 is provided instead on the tens display unit locating ledge 224 of the chassis frame 204 (FIG. 11). The design provides for the boss 241 to sit close to the actuator valve stem post of the inhaler (not shown) when the dose counter is assembled into the inhaler.

The units display unit 233 has a single set of gear teeth 238, corresponding to the indexing teeth 38 (see e.g. FIG. 1), that also serve to engage a non-return arm 208 and so also act as non-return teeth. When it is assembled into the chassis 202, the units display unit 233 is retained on the chassis 202 because the non-return arm 208 goes around the units display unit 233 and engages the gear teeth 238.

During a return stroke, the drive pawl 206 must ride over a tooth while the non-return arm 208 prevents the units display unit 233 from rotating backwards. The gear teeth 238 are shaped such that the long side of each tooth has a convex surface. The component of force from the flexing drive pawl 206 that acts to resist return of the displacement plate 219 is thereby reduced later in the travel when the force applied by the spring arms 212 is reducing: return is less hindered by the drive pawl 206 having to ride over a gear tooth with a convex surface.

The chassis 202 has downwardly directed legs 247 on either side of the chassis and integrally formed with it, for precisely positioning the dose counter in an inhaler actuator. The legs have vertical grooves 248, which may engage internal vertical ribs of the actuator to prevent any rotational movement of the dose counter. The legs have feet 249 that are turned inwards to form clips that locate in recesses located on the floor of a pMDI actuator (not shown). Alternatively, the feet may locate on top of ribs or other features in the actuator. The dose counter may advantageously be located in the actuator by an interference (friction) fit; alternatively clipping features may be provided.

Figure 10:
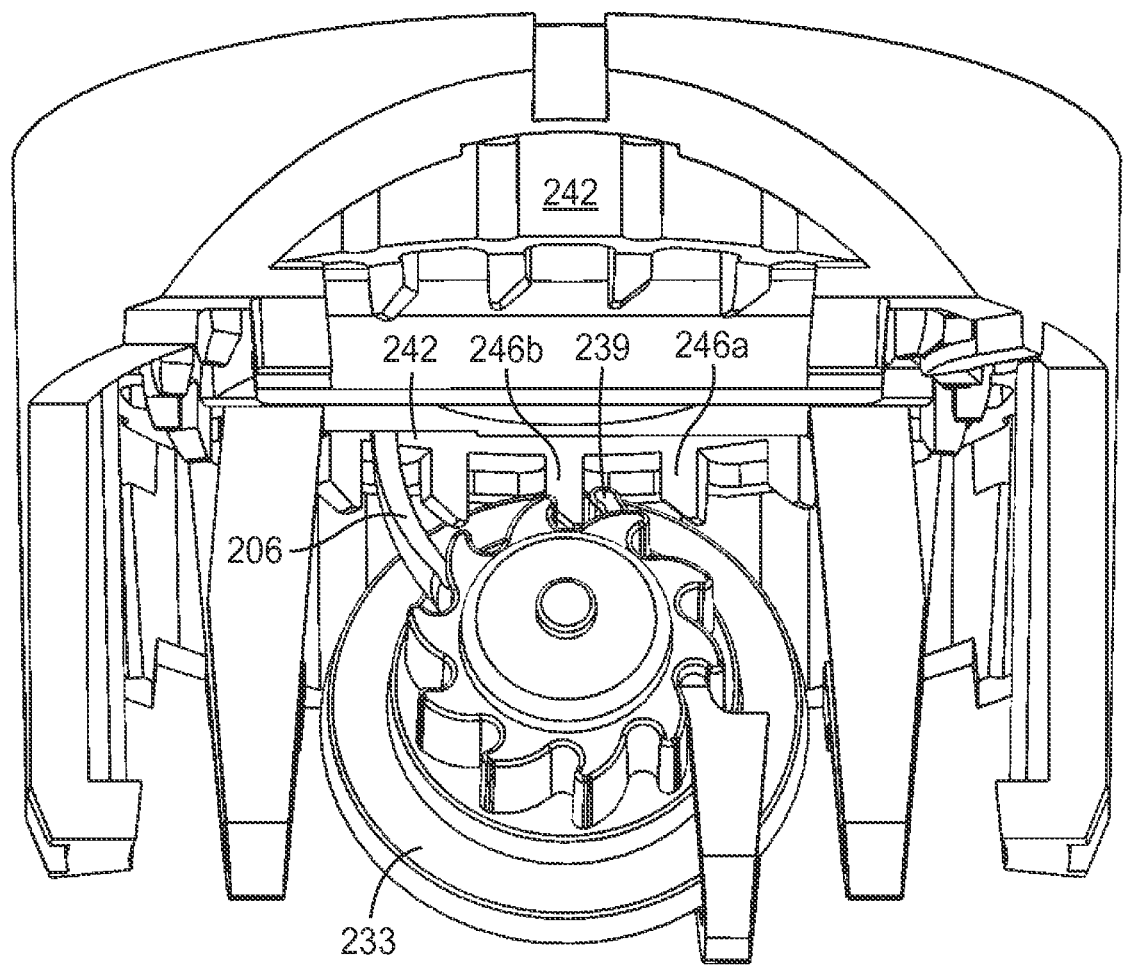
FIG. 10 shows another bottom perspective view of the third exemplary dose indicator.

FIG. 10 shows a view in which the tens display unit drive tooth 239 is about to engage a tens display unit indexing tooth 246b. The angled forward surface of each indexing tooth 246 combined with the relative planes in which the tens display unit 242 and units display unit 233 lie, ensure that the tens display unit drive tooth 239 has clearance whilst having an adequate vertical rear surface of the indexing tooth 246b to engage with to rotate the tens display unit 242 to just past the desired amount. Thence the tens display unit non-return arm 228 (not visible in FIG. 10: see FIG. 9) will adjust the position of the tens display unit, e.g. by slight back rotation, to align indicia thereon with the viewing cut out 230 (see FIG. 2 for the corresponding part 30).

FIG. 11 shows zero stop arm 216 of the chassis 202 engaging the zero stop 244 of the tens display unit 242. Once this point of travel is reached, a further count of nine can be made on the units display unit 233. After that, the tens display unit drive tooth 239 is stopped by the last indexing tooth 246, and the units display unit 233 can no longer rotate. Downward movement of the displacement plate 219 causes the drive pawl 206 to engage a tooth 238 that does not move, due to the stopping of the tens display unit. Under this load, the drive pawl 206 deflects allowing additional doses to be taken upon this and subsequent actuations with minimal additional resistance to actuation. The drive pawl 206 is angled (relative to a vertical line) both away from the axis of the hinges 220 and also inwardly towards the axis of the tens display unit 242.

Figure 12A:
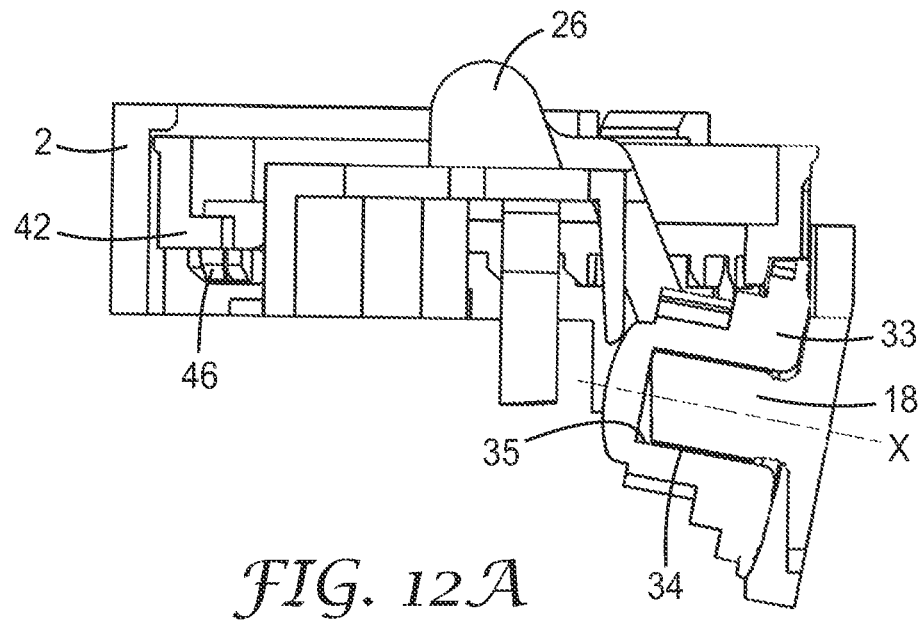
FIGS. 12a and 12b show vertical cross sections, taken centrally through the back and front of each dose indicator, of the dose indicator of FIGS. 1 to 7 and a similar, alternative embodiment respectively.
Figure 12B:
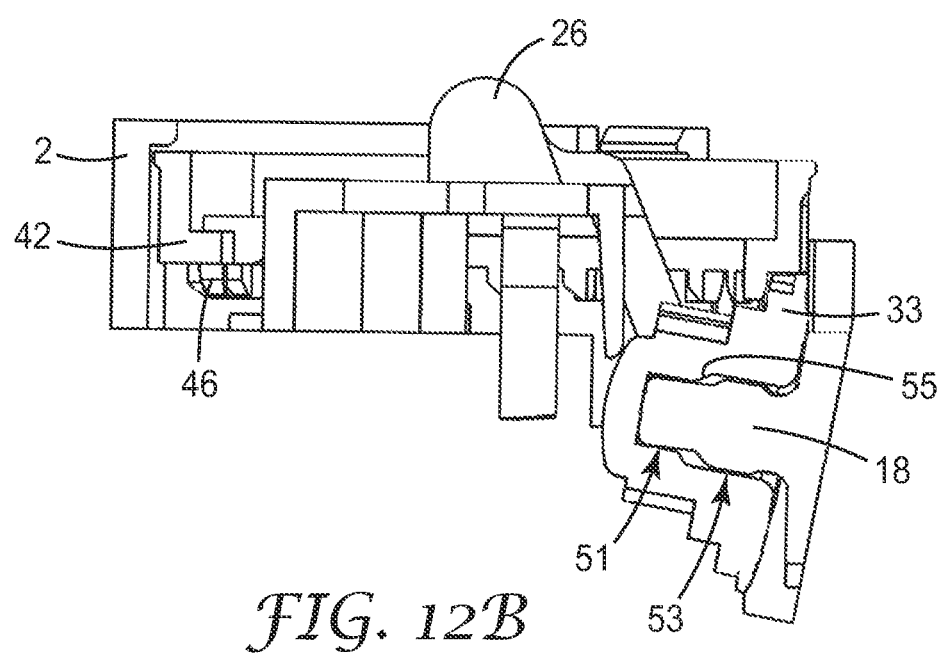

FIGS. 12a and 12b respectively show the embodiment of FIGS. 1 to 7 and an alternative embodiment, similar except in the detail of the mounting means for mounting the units display unit. FIG. 12a shows the units display unit 33, the units display unit axle 18 and the axis of the axle X. The external surface of the axle is shown in close engagement with the internal surface 35 of the units display unit axle bearing 34, for a substantial part of the length of the axle bearing. FIG. 2 shows that one side of the axle 18 has a flat, which avoids the possibility of compressing air between the axle and bearing during assembly and thereby making them susceptible to separation. In FIG. 12b, the units display unit axle 18 has two circumferential engagement surfaces 51, 53 for engagement, at least for most of the circumference, with an internal double-cylindrical profile 55 of the units display unit 33. The two surfaces are separated along the axis of the axle 18 to provide stability against wobble. A slight lead-in (e.g. a radiussed or chamfered edge) is provided on the distal end (the end that is engaged deepest into the units display unit) of the axle 18 to help with assembly.

Figure 13:
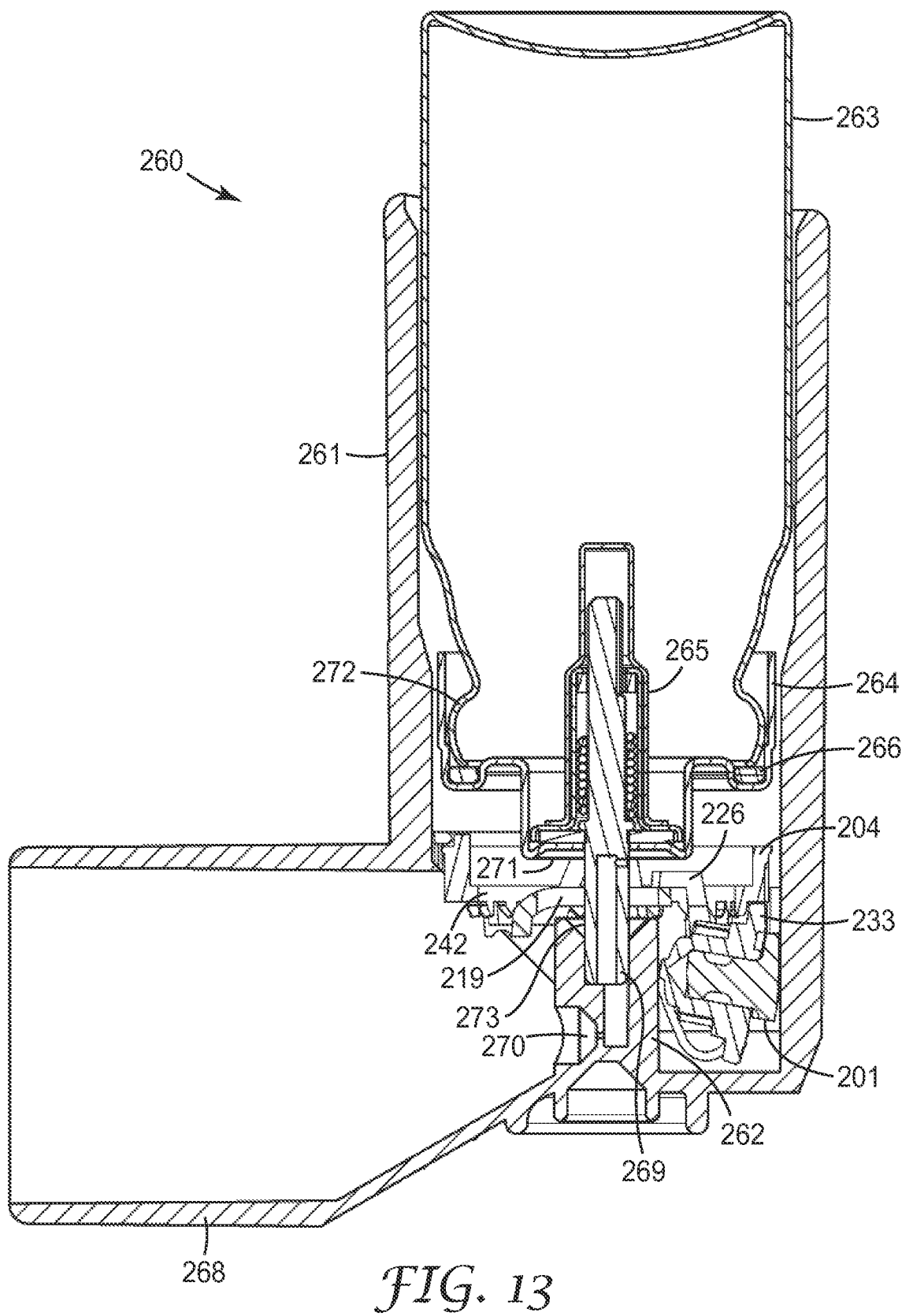
FIG. 13 shows a cross section through a pressurised metered dose inhaler incorporating a dose indicator as illustrated in FIGS. 10 and 11.

FIG. 13 shows a pressurised metered dose inhaler (pMDI) 260 comprising a canister 263 including a metered dose-dispensing valve 265 mounted via a ferrule 264 on to the neck of a vial 272 component of the canister 263 with an elastomeric gasket 266 to create a seal. The inhaler 260 comprises an actuator 261 including a mouthpiece 268 (in an alternative form, suitable for nasal drug delivery, the actuator may comprise a nosepiece rather than a mouthpiece). The canister 263 is placed within the actuator 261 by inserting the valve stem 269 of the valve 265, which protrudes outside the ferrule 264, into a stem socket 273 of a stem post 262 of the actuator 261. The valve stem 269 has a dispensing passage that allows for passage of substance from a metering chamber of the valve 265 out through the valve stem 269 and actuator mouthpiece 268 (or nosepiece) to the user. To actuate (fire) the valve 265 to deliver a dose of medicament formulation, the valve stem 269 is pushed inwardly relative to the aerosol container from its resting position, allowing formulation to pass from the canister through the valve 265 and through the actuator nozzle 270 and then out to the patient.

The actuator 261 has a dose counter 201 mounted around the stem post 262. The dose counter 201 has a units display unit 233, a tens display unit 242 a chassis frame 204 and a displacement plate 219. During actuation, the canister 263 is pressed down by the user. As the canister 263 is pressed into the actuator 261, the ferrule face 271 surrounding the valve stem 269 contacts indexing knuckles 226 and displaces the displacement plate 219. The result is that the drive pawl (206; not visible in FIG. 13) indexes the units display unit 233 in the manner described above.

The invention claimed is:

1. A dose indicator comprising,
an indexable first display unit indexable about a first display axis,
an indexable second display unit indexable about a second display axis, the second display axis being transverse to the first display axis, and
a chassis comprising a chassis frame, a displacement portion comprising a drive member to engage the first display unit, and at least one hinge directly connecting the displacement portion and chassis frame.

2. A dose indicator as claimed in claim 1, wherein the first display unit and/or the second display unit are substantially circular and are rotatably indexable about the first display axis and/or about the second display axis respectively.

3. A dose indicator as claimed in claim 1, wherein the drive pawl has an end that engages with the first display unit, said end being angled in towards the axis of rotation of said first display unit.

4. A dose indicator as claimed in claim 1, wherein the drive member is located on the displacement portion at a position remote from the hinge.

5. A dose indicator as claimed in claim 1, wherein the displacement portion comprises at least one press member.

6. A dose indicator as claimed in claim 1, wherein the first and/or the second display unit is adapted to index through between 5 and 25 indicia.

7. A dose indicator as claimed in claim 1, further comprising a first display unit mounting member for mounting the display unit on the chassis frame so that it is indexable about the first display axis.

8. A dose indicator as claimed in claim 1, wherein the first display unit is a units display unit.

9. A dose indicator as claimed in claim 1, wherein the second display unit is a tens display unit.

10. A dose indicator as claimed in claim 1, wherein the first display unit comprises a drive arm adapted to index the second display unit.

11. A dose indicator as claimed in claim 1, wherein the first display unit has a substantially circular cross section.

12. A dose indicator as claimed in claim 1, wherein the second display unit has a substantially annular cross section.

13. A dose indicator as claimed in claim 1, wherein the chassis comprises polyoxymethylene.

14. A dose indicator as claimed in claim 1, wherein the drive member is adapted to engage the first display unit.

15. A dose indicator as claimed in claim 14, wherein the drive member is adapted to engage the first display unit on a curved path, the drive member being driven by a force from outside the circumference of the first display unit.

16. A dose indicator as claimed in claim 1, wherein the displacement portion is adapted to be displaced along a displacement path.

17. A dose indicator as claimed in claim 16, wherein the displacement path is at least partly transverse to the first display axis.

18. A dose indicator as claimed in claim 16 wherein the displacement path is at least partly arcuate.

19. A dose indicator as claimed in claim 1, further comprising at least a first display non-return mechanism.

20. A dose indicator as claimed in claim 19, wherein the first display non-return mechanism comprises a non-return arm adapted to interact with one or more detents on the first display unit.

21. A dose indicator as claimed in claim 20 wherein the return mechanism comprises at least one spring.

22. A dose indicator as claimed in claim 21, wherein the at least one spring comprises a leaf spring.

23. A dose indicator as claimed in claim 21, wherein the at least one return mechanism directly or indirectly connects the displacement portion and chassis frame.

24. A dose indicator as claimed in claim 1, wherein the chassis further comprises at least one return mechanism.

25. A dose indicator as claimed in claim 24, wherein the at least one return mechanism directly or indirectly connects the displacement portion and chassis frame.

26. A dose indicator as claimed in claim 1, wherein the first and/or the second display unit comprises a zero stop member.

27. A dose indicator as claimed in claim 26, wherein the zero stop member interacts with a stop arm located on the chassis.

28. An actuator for an inhaler, the actuator comprising a dose indicator as claimed in claim 1.

29. An inhaler comprising an actuator as claimed in claim 28.

* * * * *